(12) United States Patent
Borkholder et al.

(10) Patent No.: US 12,036,044 B2
(45) Date of Patent: *Jul. 16, 2024

(54) APPARATUS, SYSTEM AND METHOD FOR MEDICAL ANALYSES OF SEATED INDIVIDUAL

(71) Applicant: Casana Care, Inc., Rochester, NY (US)

(72) Inventors: David A. Borkholder, Canandaigua, NY (US); Nicholas J. Conn, Winston Salem, NC (US); Masoumeh Haghpanahi, Rochester, NY (US)

(73) Assignee: Casana Care, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/557,264

(22) Filed: Dec. 21, 2021

(65) Prior Publication Data

US 2022/0218286 A1 Jul. 14, 2022

Related U.S. Application Data

(63) Continuation of application No. 16/377,938, filed on Apr. 8, 2019, now Pat. No. 11,234,651, which is a
(Continued)

(51) Int. Cl.
*A61B 5/11* (2006.01)
*A47K 13/24* (2006.01)
(Continued)

(52) U.S. Cl.
CPC ............ *A61B 5/6891* (2013.01); *A47K 13/24* (2013.01); *A61B 5/02028* (2013.01);
(Continued)

(58) Field of Classification Search
CPC ...... A47K 13/24; A61B 5/01; A61B 5/02028; A61B 5/02055; A61B 5/02416;
(Continued)

(56) References Cited

U.S. PATENT DOCUMENTS 4,203,497 A 5/1980 Harris et al.
4,212,361 A 7/1980 Stocker et al.
(Continued)

FOREIGN PATENT DOCUMENTS

CA 1324415 11/1993
CN 100502773 C 6/2009
(Continued)

OTHER PUBLICATIONS

Weber, Thomas, Ammer, Marcus, Rammer, Martin, Adji, Audrey, O'Rourke, Michael F., Wassertheurer, Siegfried, Rosenkranz, Stefan, and Eber, Bernd, Noninvasive determination of carotid-femoral pulse wave velocity depends critically on assessment of travel distance: a comparison with invasive measurement, Journal of Hypertension, 2009, pp. 1624-1630, vol. 27, No. 8, Lippincott Williams & Wilkins, DOI:10.1097/HJH.0b013e32832cb04e.
(Continued)

*Primary Examiner* — Jon Eric C Morales

(57) ABSTRACT

Apparatus, system and method for medical analysis of a seated individual, includes determining the aortic valve opening; the PTT; and calculating the PWV. Determining the aortic valve opening includes collecting BCG data while sitting on a seat and determining the timing of the aortic valve opening, taking into account posture. Measuring the aortic pulse wave transit time includes collecting BCG data while sitting on a seat capable of measuring changes in apparent weight; determining the timing of the aortic valve opening; detecting the arrival of the pulse wave at the end point; and measuring the relative timings of the two events. Calculating the PWV includes determining a length of the arterial segment through which a pulse wave is to be measured between a start point and an end point; and dividing the determined length of the arterial segment by the PTT.

27 Claims, 9 Drawing Sheets

Related U.S. Application Data continuation of application No. 15/190,534, filed on Jun. 23, 2016, now Pat. No. 10,292,658.

(60) Provisional application No. 62/183,222, filed on Jun. 23, 2015.

(51) Int. Cl.

| | |
|---|---|
| *A61B 5/00* | (2006.01) |
| *A61B 5/02* | (2006.01) |
| *A61B 5/0205* | (2006.01) |
| *A61B 5/318* | (2021.01) |
| *G01G 19/44* | (2006.01) |
| *G01G 19/52* | (2006.01) |
| *A61B 5/01* | (2006.01) |
| *A61B 5/024* | (2006.01) |
| *A61B 5/053* | (2021.01) |
| *A61B 5/1455* | (2006.01) |

(52) U.S. Cl.
CPC ........ *A61B 5/02055* (2013.01); *A61B 5/1102* (2013.01); *A61B 5/318* (2021.01); *A61B 5/4561* (2013.01); *A61B 5/7246* (2013.01); *G01G 19/44* (2013.01); *G01G 19/52* (2013.01); *A61B 5/01* (2013.01); *A61B 5/02416* (2013.01); *A61B 5/053* (2013.01); *A61B 5/14551* (2013.01)

(58) Field of Classification Search
CPC ... A61B 5/053; A61B 5/1102; A61B 5/14551; A61B 5/318; A61B 5/4561; A61B 5/6891; A61B 5/7246
See application file for complete search history.

(56) References Cited

U.S. PATENT DOCUMENTS

| | | | |
|---|---|---|---|
| 4,697,656 | A | 10/1987 | de Canecaude |
| 4,711,313 | A | 12/1987 | Iida et al. |
| 4,969,112 | A | 11/1990 | Castle |
| 6,727,438 | B1 | 4/2004 | Stokes |
| 7,437,781 | B2 | 10/2008 | Rigas |
| 7,521,638 | B1 | 4/2009 | Godshaw et al. |
| 8,827,918 | B2 | 9/2014 | Kim et al. |
| 8,983,854 | B2 | 3/2015 | Park |
| 9,595,185 | B1 | 3/2017 | Hall et al. |
| 9,829,311 | B1 | 11/2017 | Wilson et al. |
| 9,927,302 | B1 | 3/2018 | Hall et al. |
| 10,292,658 | B2 | 5/2019 | Borkholder |
| 11,234,651 | B2 * | 2/2022 | Borkholder ............ A47K 13/24 |
| 11,650,094 | B2 | 5/2023 | Borkholder et al. |
| 2002/0188205 | A1 | 12/2002 | Mills |
| 2003/0233034 | A1 | 12/2003 | Varri et al. |
| 2004/0112149 | A1 | 6/2004 | Gebert |
| 2005/0228305 | A1 | 10/2005 | Nagata et al. |
| 2006/0111641 | A1 | 5/2006 | Manera et al. |
| 2006/0258915 | A1 | 11/2006 | Ueda et al. |
| 2008/0194975 | A1 | 8/2008 | MacQuarrie et al. |
| 2010/0094147 | A1 | 4/2010 | Inan et al. |
| 2013/0310700 | A1 | 11/2013 | Wiard et al. |
| 2014/0039330 | A1 | 3/2014 | Seo |
| 2014/0142396 | A1 | 5/2014 | Ricks et al. |
| 2014/0142437 | A1 | 5/2014 | Inan et al. |
| 2014/0142451 | A1 | 5/2014 | Kim |
| 2016/0317043 | A1 | 11/2016 | Campo |
| 2016/0331244 | A1 | 11/2016 | Barton-Sweeney et al. |
| 2016/0374618 | A1 | 12/2016 | Giovangrandi |
| 2016/0374619 | A1 | 12/2016 | Borkholder et al. |
| 2017/0172421 | A1 | 7/2017 | Dabby et al. |
| 2018/0020984 | A1 | 1/2018 | Hall et al. |
| 2018/0042386 | A1 | 2/2018 | Hall et al. |
| 2018/0084960 | A1 | 3/2018 | Iwabata et al. |
| 2018/0153414 | A1 | 6/2018 | Hall et al. |
| 2019/0008457 | A1 | 1/2019 | Hall et al. |
| 2019/0008567 | A1 | 1/2019 | Barry |
| 2019/0178704 | A1 | 6/2019 | Lui |
| 2019/0231271 | A1 | 8/2019 | Borkholder et al. |
| 2019/0298316 | A1 | 10/2019 | Kashyap et al. |
| 2020/0289000 | A1 | 9/2020 | Hall et al. |
| 2020/0390367 | A1 | 12/2020 | Hall et al. |
| 2020/0390422 | A1 | 12/2020 | Hall et al. |
| 2022/0346720 | A1 | 11/2022 | David et al. |
| 2022/0361754 | A1 | 11/2022 | Borkholder et al. |
| 2022/0364904 | A1 | 11/2022 | Borkholder et al. |
| 2022/0378373 | A1 | 12/2022 | Borkholder et al. |
| 2023/0240485 | A1 | 8/2023 | Kashyap et al. |

FOREIGN PATENT DOCUMENTS

| | | |
|---|---|---|
| CN | 203042108 U | 7/2013 |
| CN | 102660988 B | 3/2014 |
| CN | 210 123 304 U | 3/2020 |
| DE | 102010061035 B4 | 10/2012 |
| EP | 1488739 A1 | 12/2004 |
| JP | H04-367638 A | 12/1992 |
| JP | 2000-254040 A1 | 9/2000 |
| JP | 2010-172498 A | 8/2010 |
| JP | 2020-153896 A | 9/2020 |
| KR | 2017/0125696 A | 11/2017 |
| WO | WO2005070288 A1 | 8/2005 |
| WO | WO 2020/172645 A1 | 8/2020 |
| WO | WO 2021/055681 A1 | 3/2021 |

OTHER PUBLICATIONS

Lim, Yong Gyu, Lee, Jeong Su, Lee, Seung Min, Lee, Hong Ji, and Park, Kwang Suk, Capacitive Measurement of ECG for Ubiquitous Healthcare, Annals of Biomedical Engineering, Nov. 2014, pp. 2218-2227, vol. 42, No. 11, Biomedical Engineering Society, DOI:10.1007/s10439-014-1069-6.

Chen, Zhihao, Yang, Xiufeng, Teo, Ju Teng, and Ng, Soon Huat, Noninvasive Monitoring of Blood Pressure Using Optical Ballistocardiography and Photoplethysmograph Approaches, 35th Annual International Conference of the IEEE EMBS, Jul. 3-7, 2013, pp. 2425-2428, Osaka, Japan.

Park, Kwang Suk, Nonintrusive Measurement of Biological Signals for Ubiquitous Healthcare, 31st Annual International Conference of the IEEE EMBS, Sep. 2-6, 2009, pp. 6573-6575, Minneapolis, Minnesota, USA.

Kim, J.S., Park, J.W., Ryu, M.S., and Park, K.S., Multi-channel measurement of photo-plethysmography and evaluation for the optimal site of a thigh in a toilet, Proceedings of the 26th Annual International Conference of the IEEE EMBS, Sep. 1-5, 2004, pp. 3366-3368, San Francisco, California, USA.

Yamakoshi, K.,Kuroda, M., Tanaka, S., Yamaguchi, I., and Kawarada, A., Non-conscious and Automatic Acquisition of Body and Excreta Weight Together with Ballistocardiogram in a Lavatory, 18th Annual International Conference of the IEEE Engineering in Medicine and Biology Society, 1996, pp. 67-68, Amsterdam, 1.1.6: Home Health Monitoring.

Tanaka, Shinobu, Nogawa, Masamichi, and Yamakoshi, Ken-ichi, Fully Automatic System for Monitoring Blood Pressure from a Toilet-Seat Using Volume-Oscillometric Method, Proceedings of the 2005 IEEE Engineering in Medicine and Biology 27th Annual Conference, Sep. 1-4, 2005, pp. 3939-3941, Shanghai, China.

Huang, Ji-Jer, Yu, Sheng-I, and Syu, Hao-Yi, Development of the smart toilet equipment with measurements of physiological parameters, 2012 9th International Conference on Ubiquitous Intelligence and Computer and 9th International Conference on Autonomic and Trusted Computing, 2012, pp. 9-16, DOI: 10.1109/UIC-ATC.2012.143.

Schlebusch, T., Unobtrusive Health Screening on an Intelligent Toilet Seat, ACTA Polytechnica, pp. 94-99, vol. 51, No. May 2011, http://www.tk.de/tk/innovative-verfahren/telemedizin/herz/9784.

Motoi, Kosuke, Ogawa, Mitsuhiro, Ueno, Hiroshi, Fukunage, Seiji, Yuji, Tadahiko, Higashi, Yuji, Tanaka, Shinobu, Fujimoto, Toshiro, Asanoi, Hidetsugu, and Yamakoshi, Ken-ichi, Development and

(56) References Cited

OTHER PUBLICATIONS

Clinical Evaluation of a Home Healthcare System Measuring in Toilet, Bathtub and Bed without Attachment of Any Biological Sensors, IEEE, 2010.

Motoi, K., Kubota, S., Ikarashi, A., Nogawa, M., Tanaka, S., Nemoto, T., and Yamakoshi, K., Development of a fully automated network system for long-term health-care monitoring at home, Proceedings of the 29th Annual International Conference of the IEEE EMBS, Aug. 23-26, 2007, pp. 1826-1829, Cite Internationale, Lyon, France.

Shin, J.H., Chung, G.S., Kim, K.K., Kim, J.S., Hwang, B.S., Park, K.S., Ubiquitous House and Unconstrained Monitoring Devices for Home Healthcare System, 6th International Special Topic Conference on ITAB, 2007, Tokyo.

Togawa, Tatsuo, Tamura, Toshiyo, Zhou, Jianxin, Mizukami, Hiroshi, and Ishijima, Masayuki, Physiological Monitoring Systems Attached to the Bed and Sanitary Equipments, IEEE Engineering in Medicine & Biology Society 11th Annual International Conference—1461, 1989.

Baek, Hyun Jae, Kim, Jung Soo, Kim, Ko Keun, and Park, Kwang Suk, System for Unconstrained ECG Measurement on a Toilet Seat using Capacitive Coupled Electrodes: The Efficacy and Practicality, 30th Annual International IEEE EMBS Conference, Aug. 20-24, 2008, pp. 2326-2328, Vancouver, British Columbia, Canada.

Kim, Jung Soo, Chee, Young Joon, Park, Ju Wan, Choi, Jin Wook, and Park, Kwang Suk, A new approach for non-intrusive monitoring of blood pressure on a toilet seat, Physiological Measurement, 2006, pp. 203-211, vol. 27, IOP Publishing Ltd, United Kingdom.

Kim, Ko Keun, Lim, Yong Kyu, and Park, Kwang Suk, The Electrically Non-contacting ECG Measurement on the Toilet Seat Using the Capacitively-coupled Insulated Electrodes, Proceedings of the 26th Annual International Conference of the IEEE EMBS, Sep. 1-5, 2004, pp. 2375-2378, San Francisco, CA, USA.

Inan, O.T., Etemadi, M., Wiard, R.M., Giovangrandi, L., and Kovacs, G.T.A., Robust Ballistocardiogram Acquisition for Home Monitoring, Physiological Measurement, 2009, pp. 169-185, vol. 30, Institute of Physics and Engineering in Medicine, United Kingdom.

Junnila, Sakari, Akhbardeh, Alireza, Varri, Alpo, and Koivistoinen, T., An EMFi-film Sensor based Ballistocardiographic Chair: Performance and Cycle Extraction Method, IEEE Workshop on Signal Processing Systems Design and Implementation, 2005, pp. 373-377, IEEE.

Prisk, G.K., Verhaeghe, S., Padeken, D., Hamacher, H., and Paiva, M., Three-Dimensional Ballistocardiography and Respiratory Motion in Sustained Microgravity, Aviation, Space, and Environmental Medicine, Dec. 2001, pp. 1067-1074, vol. 72, No. 12.

Javaid, Abdul Qadir, Wiens, Andrew D., Fesmire, Nathaniel Forrest, Weitnauer, Mary Ann, and Inan, Omer T., Quantifying and Reducing Posture-Dependent Distortion in Ballistocardiogram Measurements, IEEE Journal of Biomedical and Health Informatics, Sep. 2015, pp. 1549-1556, vol. 19, No. 5.

Tavakolian, K., Ngai, B., Akhbardeh, A., Kaminska, B., Blaber, A., Comparative Analysis of Infrasonic Cardiac Signals, Computers in Cardiology, 2009, pp. 757-760, vol. 36, ISSN 0276-6574.

Arias, Diego E., Pino, Esteban J., Aqueveque, Pablo, and Curtis, Dorothy W., Data Collection Capabilities of a New Non-Invasive Monitoring System for Patients with Advanced Multiple Sclerosis, AMIA Annual Symposium Proceedings, vol. 2013, American Medical Informatics Association.

Advisory Action for U.S. Appl. No. 15/190,534 (mailed Nov. 13, 2018).

Final Office Action for U.S. Appl. No. 15/190,534 (mailed Sep. 4, 2018).

Non Final Office Action for U.S. Appl. No. 15/190,534 (mailed Feb. 22, 2018).

Final Office Action for U.S. Appl. No. 15/190,534 (mailed Oct. 6, 2017).

Non Final Office Action for U.S. Appl. No. 15/190,534 (mailed Jan. 26, 2017).

Final Office Action for U.S. Appl. No. 16/377,938 (mailed May 5, 2021).

Non Final Office Action for U.S. Appl. No. 16/377,938 (mailed Dec. 1, 2020).

Non Final Office Action for U.S. Appl. No. 16/377,938 (mailed Jul. 6, 2020).

Non-Final Office Action mailed Jul. 17, 2023 for U.S. Appl. No. 17/885,299, 31 pages.

Final Office Action for U.S. Appl. No. 17/885,299 dated Dec. 21, 2023, 12 pages.

Non-Final Office Action for U.S. Appl. No. 17/851,938 mailed on Mar. 10, 2023, 21 pages.

Final Office Action for U.S. Appl. No. 17/851,938 dated Jun. 28, 2023, 22 pages.

\* cited by examiner

APPARATUS, SYSTEM AND METHOD FOR MEDICAL ANALYSES OF SEATED INDIVIDUAL

CROSS REFERENCE

This application is a Continuation of U.S. Non-Provisional application Ser. No. 15/190,534, filed on Jun. 23, 2016, which claims the benefit of the filing date of U.S. Provisional Patent Application Ser. No. 62/183,222, filed Jun. 23, 2015, which is hereby incorporated by reference in its entirety.

FIELD

The disclosure relates to apparatus, system and method for medical analyses of a seated individual, and in specific instances for detecting heart function and processing signals therefrom.

BACKGROUND

Existing methods for tracking an individual's vital signs involves either taking time out of their day to use medical devices, or wearing portable ambulatory devices. These methods are intrusive to one's daily life, requiring one to change their lifestyle and habits in order to consistently acquire their medical state.

Historically, there are four measurement techniques that are used for estimation of a pulse wave velocity. First, the clinical gold standard uses tonometry where a transducer is held against the carotid artery (neck) and a thigh pressure cuff is used to measure when the pulse wave reaches the femoral artery. The distance between the two measurement points, coupled with the pulse transit time (PTT) is used to determine an aortic pulse wave velocity (PWV) and estimate aortic compliance. This method requires assistance from medically trained personnel to provide and properly attach the equipment to the patient.

In a second technique, two points on the same artery are used to measure an arterial PTT, with the distance between measurement points determining PWV. This is often done using two photoplethysmography (PPG) sensors with known separation between the two positioned on the radial artery of the arm, or in the finger (using the foot to foot measurement of the two PPG waveforms). However, this technique estimates the PWV in the measured peripheral artery, not in the aorta, and is therefore not useful for determining aortic compliance, but is often used to estimate blood pressure.

In a third technique, the R-wave peak of the ECG is used as the starting point, with a peripheral PPG measurement (often finger, toe, or ear) used as the distal point. This measurement is called the pulse arrival time (PAT) and is often used as a surrogate for PTT (and PWV) in estimating blood pressure. However, as this measurement technique includes the PEP it has no basis in physiology and fundamental pulse wave velocity/blood pressure theory.

In a fourth technique, the BCG is used as the starting point (estimating aortic ejection) and PPG at the periphery (toe) is used as the distal point for estimation of a PWV. This approach measures an averaged PWV of the aorta and femoral artery. It has been used for aortic compliance estimation. However, it is not an accurate measurement of the true aorta PWV due to the contribution of the femoral artery distance from the end of the aorta to the toe.

Chair-based approaches for recording BCG are known to produce waveforms for the same person that are significantly different for various segments of the same recording, severely reducing the diagnostic value of the measurement. Body movements are known to generate stronger signal values than normal cardiac activities during recording causing loss of information and destroying individual BCG cycles.

Currently, the art lacks integration of physiological monitoring into an individual's everyday life without causing them to change their habits or perform any specific task. The art further lacks health condition monitoring techniques that provide a robust measure of aortic PWV without the aid of medical personnel for collection of data. The art lacks the ability for the daily non-invasive medical analysis of the cardiac and vascular functions of an individual.

SUMMARY

In accordance with one aspect of the present disclosure a method for determining the aortic valve opening of a seated individual includes recording the BCG of the individual while sitting on a seat having a force sensor capable of measuring changes in the apparent weight of the seated individual; and detecting a location on the recorded BCG waveform or its transforms representing the aortic valve opening indicating ventricular ejection and the origination of a pulse wave taking into account the posture of the seated individual.

In accordance with another aspect the present disclosure further includes determining the PTT of the seated individual by determining the time of aortic valve opening; detecting the arrival of the initiated pulse wave at the end point while sitting on the seat; and measuring the relative timings of the two events.

In accordance with another aspect the present disclosure further includes calculating the PWV of the seated individual by dividing the determined length of the arterial segment by the pulse transit time from the initiation at the start point to the detection at the end point of the pulse.

In accordance with another aspect of the present disclosure a method for medical analysis of a seated individual includes collecting BCG data over time from the individual while sitting on a seat comprising at least one force sensor capable of measuring changes in the apparent weight of the seated individual; and determining the timing of the aortic valve opening from the BCG data taking into account the angle between the seat platform and the torso of the seated individual.

In accordance with another aspect of the present disclosure a method for medical analysis of a seated individual further includes determining a selected end point along a length of artery from the aortic valve; detecting the arrival of the pulse wave initiated by the aortic valve opening at the selected end point along the artery while sitting on the seat; and determining the PTT of the seated individual by measuring the relative timings of the aortic valve opening and the arrival of the pulse wave at the selected end point In accordance with another aspect of the present disclosure a method for medical analysis of a seated individual further includes determining a length of the arterial segment between the aortic valve and the selected end point along the artery through which the pulse wave is measured and calculating the PWV of the seated individual by dividing the determined length of the arterial segment by the PTT In accordance with another aspect of the present disclosure a method for measuring physiological changes associated with a simulated Valsalva maneuver includes determining a length of an arterial segment along an artery from the aortic valve through which a pulse wave is to be measured between a start point representing the aortic valve opening and an end point; during a BM detecting the aortic valve opening indicating ventricular ejection of the origination of a pulse wave by recording the bBCG of the individual while sitting on a toilet seat having a force sensor capable of measuring changes in the apparent weight of the seated individual, wherein the toilet seat is secured to a toilet; detecting the arrival at the end point of the initiated pulse wave of the individual while sitting on the toilet seat; measuring the relative timings of the two events; and determining at least one physiological condition of the individual associated with the simulated Valsalva maneuver.

These and other aspects of the present disclosure will become apparent upon a review of the following detailed description and the claims appended thereto.

BRIEF DESCRIPTION OF THE DRAWINGS

The disclosure may be more completely understood in consideration of the detailed description of various embodiments of the disclosure that follows in connection with the accompanying drawings, in which.

DETAILED DESCRIPTION

Figure 1:
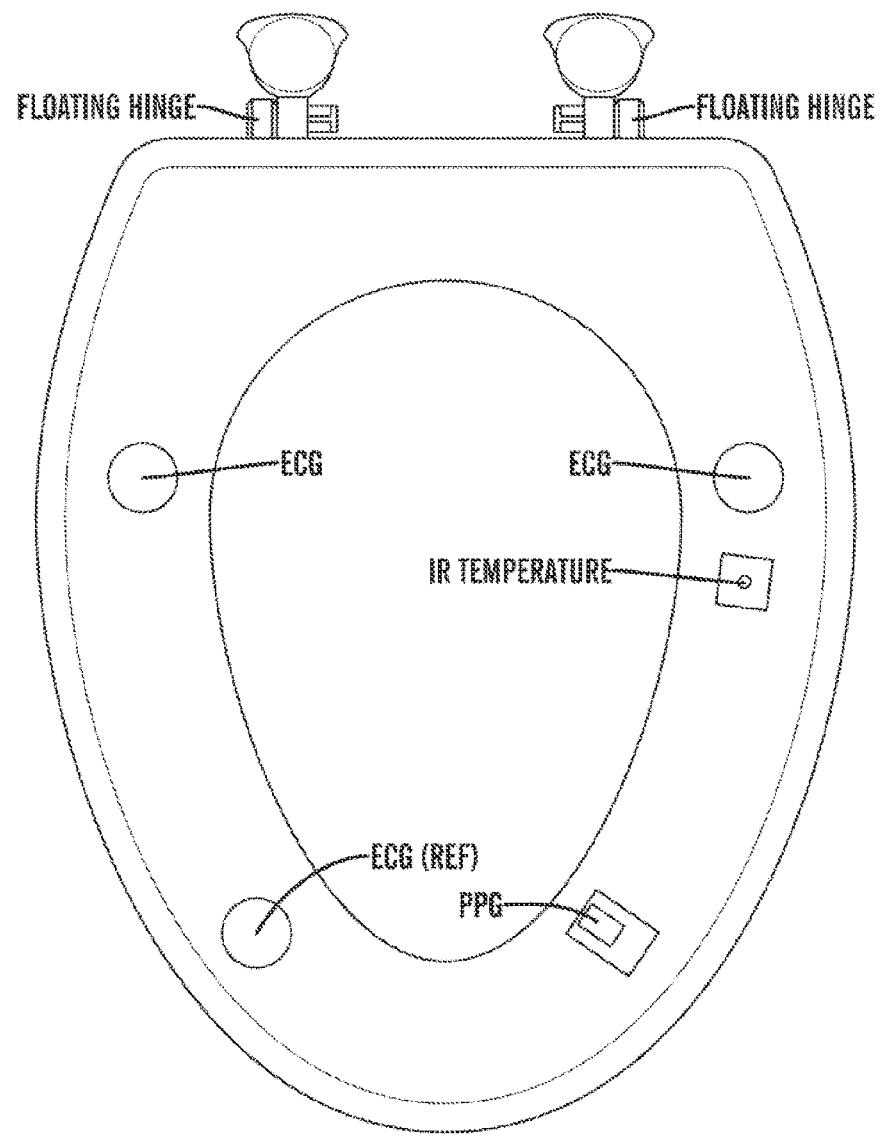
FIG. 1 illustrates a top view of an integrated toilet seat in accordance with an embodiment of the present disclosure.

The present disclosure relates to a system, method, and apparatus for the non-invasive medical analysis of an individual in a sitting position. Various embodiments illustrate the usefulness of application for daily non-invasive medical analysis of cardiac and vascular functions. An embodiment of the present disclosure includes the non-invasive medical analysis of an individual in a sitting position. BCG data is extracted from a seated individual. A suitable seat is in communication with instrumentation to extract BCG data, such as a BCG waveform, from the seated individual. A suitable seat includes a toilet seat integrated with such instrumentation. While the present disclosure is not necessarily limited to the embodiments shown herein, various aspects of the disclosure may be appreciated by those of skill in the art.

Keys to successful monitoring and early detection of changes associated with emerging or deteriorating health conditions include ensuring patient compliance, daily measurement, and consistent physiological state at the time of measurement. An embodiment of the system includes an integrated seat capable of inconspicuous daily monitoring of cardiac and vascular functions through methods including the ECG, BCG, and PPG from the buttocks or upper thigh (bECG, bBCG, and bPPG) and a base station for collection of data. In an embodiment, the seat contains sensors, microprocessor, wireless communication capabilities, and can harvest energy from the environment with techniques such as RF energy harvesting with a rectenna based system providing a self-contained bioinstrumentation system that automatically captures medically relevant data daily. Instruments such as ECG require skin contact to achieve robust measurement and can further ensure fine features of the waveform are accurately captured. Sensors which do not require skin contact are also suitable for use in the present disclosure. Additionally, the pressure associated with daily bowel movements provides opportunities for monitoring associated physiological differences between the resting state and the pressure state. Biometric analysis (e.g., ECG-based) can be used to discriminate between subjects. Data collected by the system can be used in conjunction with other bathroom and home environmental sensors to provide a broad picture of health-relevant activities and stressors.

An embodiment of the system includes a self-contained seat containing energy storage, such as a rechargeable or non-rechargeable battery. A microprocessor can provide full system control including power management, data capture, analysis and storage, and wireless communication with the base station. The base station for collection of data may be a stand-alone system or part of a larger home environmental monitoring system.

The following abbreviations and definitions are used throughout the disclosure:
  ECG—Electrocardiogram.
  PPG—Photoplethysmogram.
  BCG—Ballistocardiogram.
  bBCG—BCG is the measurement of the BCG of an individual while in the sitting position.
  bPPG—PPG is the measurement of the PPG of an individual while in the sitting position.
  bECG—ECG is the measurement of the ECG of an individual while in the sitting position.
  PTT—Pulse transit time (travel time of pressure wave in the arterial segment length of interest).
  PEP—Pre-ejection period (isovolumetric contraction of the ventricle; time between ECG Q-wave and opening of aortic valve).
  PAT—Pulse arrival time (PEP+PTT).
  PWV—Pulse wave velocity (arterial segment length divided by PTT).
  BP—Blood pressure.
  BM—Bowel movement.
  IPG—Impedance plethysmogram.
  LVET—Left ventricular ejection time.

In accordance with an embodiment of the present disclosure a method for medical analysis of a seated individual includes collecting BCG data over time and determining the timing of the opening of the aortic valve from the BCG data taking into account posture. In an embodiment, the method further includes selecting an end point along a length of artery from the aortic valve and determining the timing of a pulse wave initiated by the aortic valve opening reaching the end point. In an embodiment, measuring the aortic pulse wave velocity of an individual includes determining the length of the arterial segment between the aortic valve and the selected ending point through which the pulse wave is to be measured. The aortic valve opening indicates ventricular ejection of blood and the origination of a pulse wave associated with the ejection. This origination signal can be detected, for example, by recording the BCG of the individual while sitting on a surface in communication with a sensor capable of measuring changes in the apparent weight of the seated individual. These forces act to dynamically increase or decrease the load on the sensors and are typically in the 1 Newton range. A signal representing the arrival of the initiated pulse wave of the seated individual at the selected end point can be detected, for example, by a sensor positioned under the buttocks or upper thigh of the individual. The relative timings of the two signals can be measured, the difference being the PTT. The aortic pulse wave velocity is calculated by dividing the determined length of the arterial segment traveled by the pulse wave by the transit time from the initiation to the detection of the pulse wave, i.e., from the selected starting point to the selected ending point.

The BCG data can be represented as the BCG waveform, or a transformed BCG such as the $1^{st}$, $2^{nd}$, $3^{rd}$, etc. derivatives or integrals. The shape of the bBCG waveform measured in accordance with the present disclosure is affected by the posture of the seated individual. Therefore, it is important to be able to determine the location on the waveform that represents the opening of the aortic valve taking into account the posture or changes in posture of the seated individual. Optionally, an ECG can be used to determine a window in the bBCG waveform that contains the location of the starting point, i.e., the initiation of the pulse wave. The origination of the pulse wave can be determined in accordance with the present disclosure while accounting for posture.

An embodiment of the disclosure includes an integrated toilet seat placed on a standard toilet. Sensor systems can be integrated within the toilet seat to monitor the following: Ballistocardiogram (BCG)—measures small changes in an individual's apparent weight due to the mechanical motion of the heart; Photoplethysmogram (PPG)—an optical measure of the change in blood volume in localized tissue; Electrocardiogram (ECG)—a measure of the electric activity of the heart; $SpO_2$; body weight; and body temperature.

An embodiment of the system can enable a broad range of daily measurements extracted from the bECG, bBCG, and bPPG including: heart rate; heart rate variability; left ventricular ejection time; pulse transit time based on ECG R-wave or the BCG ejection (correlation to vascular compliance); blood pressure; cardiac output; cardiac contractility; abnormal heart function or issues with autonomic nervous control of the heart (Valsava maneuver); blood oxygenation ($SpO_2$ via filtered PPG sensors); respiration rate (IPG or PPG); stress levels (e.g., via heart rate variability); body weight; body temperature; QT interval (time between Q and T waves of the ECG); QRS duration (time from the Q wave to the T wave); PTT; PWV; PAT; LVET; and PEP.

In an embodiment, a standoff is a component that supports the seat on a base surface. The load is supported by the standoff and a sensor can be integrated with the standoff by which static and dynamic loads can be measured. In one embodiment, the integrated toilet seat has a plurality of standoffs that support the seat on the toilet surface and a pair of non-load bearing floating hinges that allow the entire seat to move vertically in both directions (e.g., up and down). This ensures each standoff is in contact with the toilet surface and can produce accurate readings from a sensor associated with the standoff.

Each standoff can have an integrated force sensor or plurality of force sensors associated with the standoff, which can measure both the subject's weight and small apparent changes in the subject's weight (e.g., measurement of the bBCG). The standoff can be a floating sealed assembly. In one embodiment, the bBCG is measured by a plurality of independent sensors (one in each standoff) positioned in a manner sufficient to determine the initiation of a pulse wave from ventricular ejection of blood from the heart regardless of the posture of an individual sitting on the integrated toilet seat. In one embodiment, the bBCG is measured with four independent sensors (one in each standoff), however other configurations can be used, such as three independent sensors (one in each standoff) (e.g., with one or two sensors on the rear standoffs), or more. Suitable sensors are capable of measuring a small change in force for monitoring the bBCG and include piezo resistive sensors, piezoelectric elements, strain gauges, or the like.

The PPG can be measured at a distal point, such as the toe or finger. For example, the PPG can be measured by an optical sensor, which typically is composed of an LED light source and a photodetector, located on the surface of the toilet seat positioned under the seated individual's buttock or upper thigh. In another embodiment, the PPG can be measured at the individual's toe from a mat or other device. The LED light source is typically green, red or IR. The photodetector is typically a photodiode or a phototransistor. The resulting waveform shows how the local blood volume changes due to the pumping of the heart, as seen in the image shown in FIGS. 7 and 8.

The ECG instrument can be positioned on the surface of the toilet seat so as to be in contact with the seated individual's skin. Typically, an ECG instrument is composed of at least three electrodes. Two of the electrodes are used for a differential measurement, while the third is a reference electrode. The reference electrode is typically driven either with the common mode signal of the other two electrodes, or a fixed reference voltage, or is referenced to ground through an impedance network. The ECG instrument may also be composed of only two differential leads.

A method for determining the aortic valve opening of a seated individual includes recording the BCG of the individual while sitting on a seat having a plurality of standoffs resting on a support surface and having a force sensor capable of measuring changes in the apparent weight of the seated individual integrated into at least one of the plurality of standoffs; and detecting a location on the BCG data representing the signal of the aortic valve opening indicating ventricular ejection of the origination of a pulse wave taking into account the posture of the seated individual.

A method for measuring the aortic pulse wave transit time of a seated individual includes determining a length of the arterial segment through which a pulse wave is to be measured between a start point representing the aortic valve opening and a selected end point along the arterial segment; recording the BCG of the individual while sitting on a seat having a force sensor capable of measuring changes in the apparent weight of the seated individual integrated into at least one of a plurality of standoffs, wherein the standoffs are resting on a support surface; detecting a location on the BCG data representing the aortic valve opening indicating ventricular ejection of a pulse wave at the start point of the seated individual; detecting a signal representing the arrival of the initiated pulse wave of the individual at the end point while sitting on the seat; and measuring the relative timings of the two events to determine the pulse transit time from the initiation at the start point to the detection at the end point of the pulse.

Figure 2:
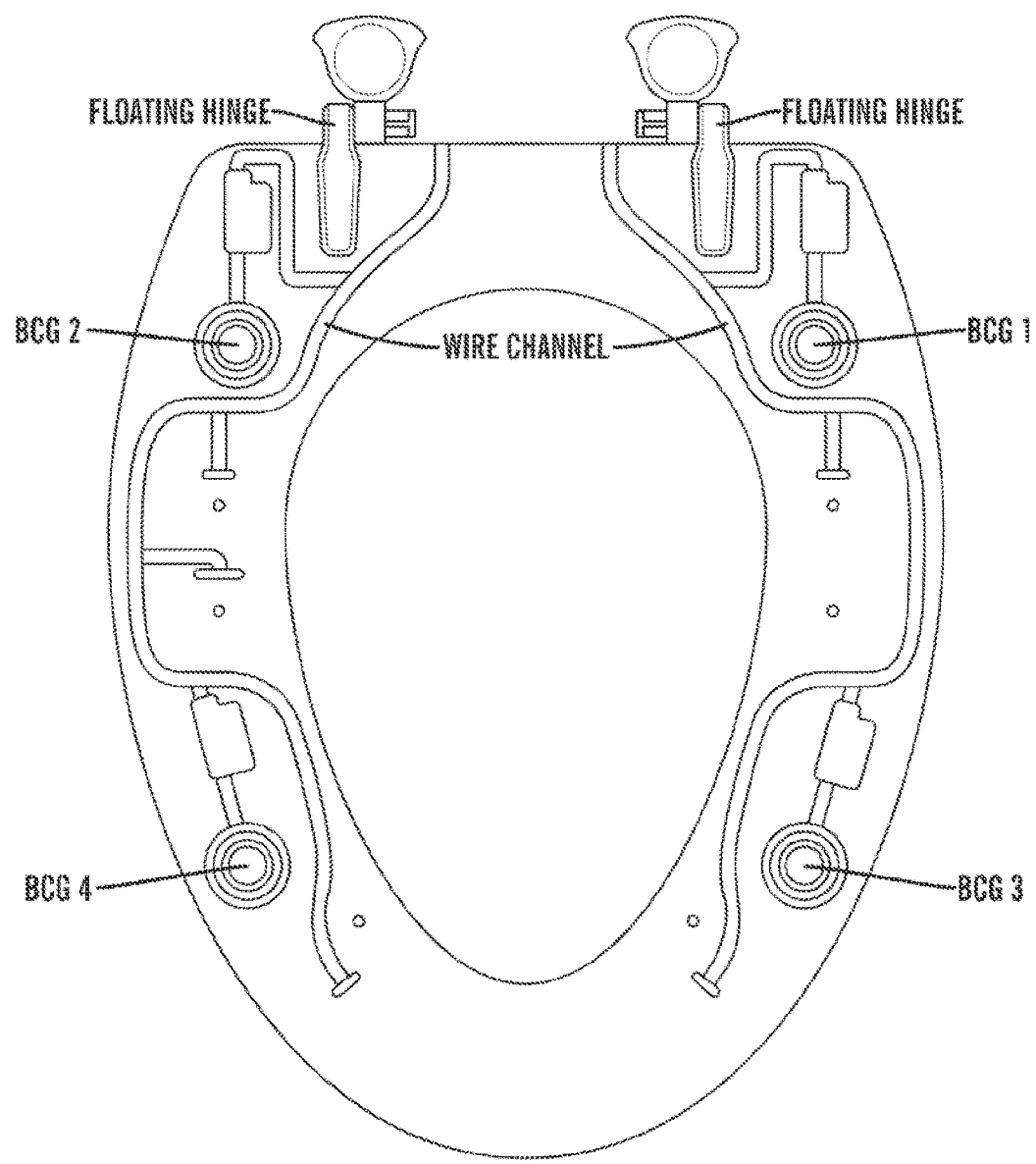
FIG. 2 illustrates a bottom view of an integrated toilet seat in accordance with an embodiment of the present disclosure.

FIG. 1 illustrates a top view of an integrated toilet seat in accordance with an embodiment of the present disclosure. FIG. 2 illustrates a bottom view of an integrated toilet seat in accordance with an embodiment of the present disclosure.

Aortic compliance and blood pressure of an individual can be derived from the Pulse Wave Velocity (from bBCG to bPPG). In an embodiment, the disclosure includes a method for the measurement of the PWV of an individual sitting on the integrated toilet seat.

Figure 3:
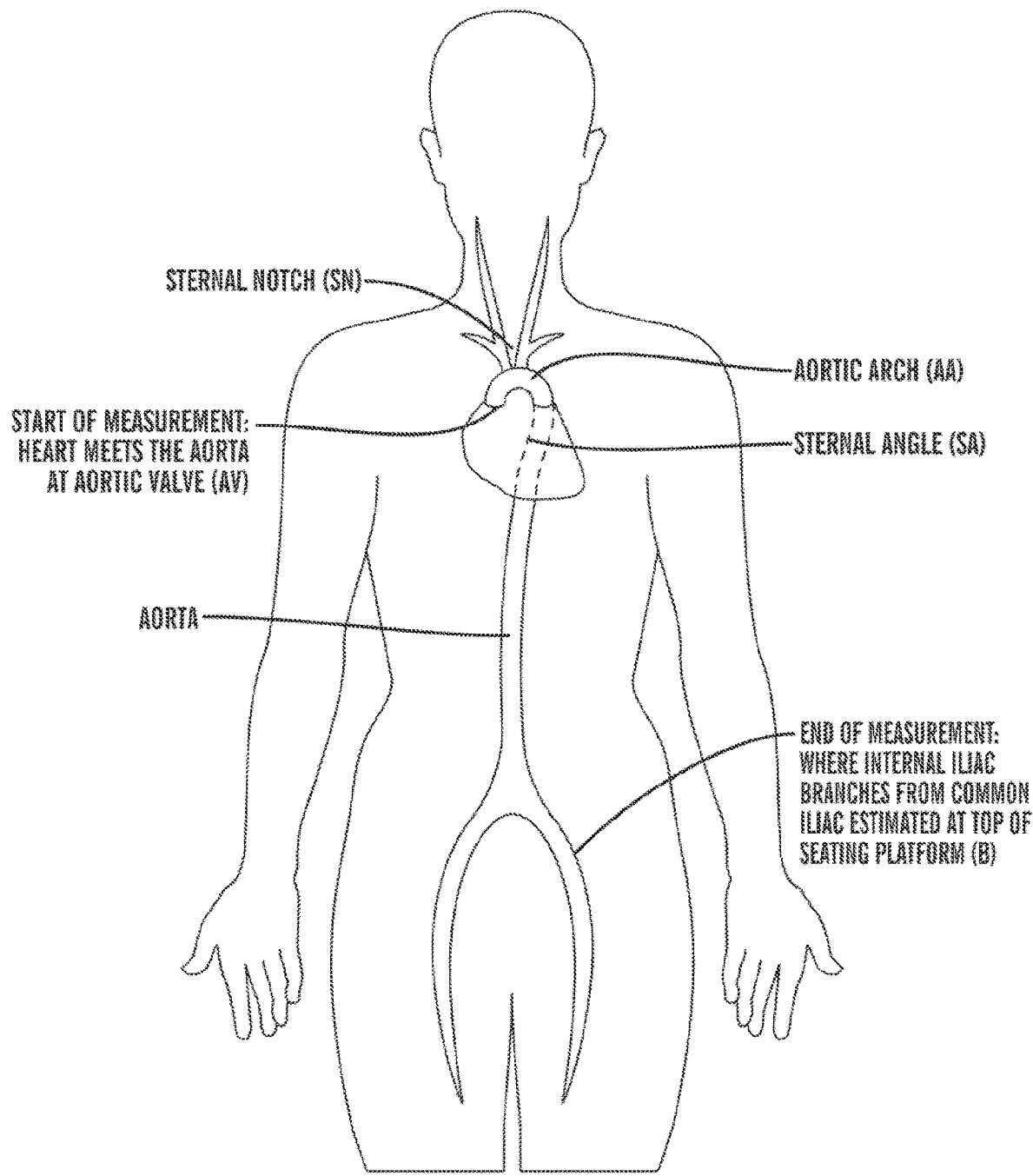
FIG. 3 is a diagram depicting the aorta and associated arteries of an individual illustrating starting and ending locations for the measurement of PTT in accordance with an embodiment of the present disclosure.

The aortic PWV can be calculated by determining the length of the arterial segment divided by the pulse transit time (PTT) over that length. The velocity is the distance divided by the time. The PTT is determined by the start of ventricular ejection (when the aortic valve opens), as well as the point in time when the pulse wave reaches the end point, for example, as shown in FIG. 3.

The BCG data can be used to determine when the heart valve opens. The start of the PTT can be identified, for example, on the BCG waveform. The PPG measures the change in local blood volume so a PPG sensor positioned under the buttocks of the seated individual can determine the end point of the PTT based on the onset of the PPG.

The pulse transit time is calculated directly by taking the difference in time between the PPG beat onset, and the aortic valve opening (AV), determined from the BCG data, as shown in the following formula.

$$PTT = \Delta t_{BCG \rightarrow PPG} = t_{PPG} - t_{AV}$$

The length of the arterial segment can be determined by various methods, including direct subject measurement on a user by user basis. However, it is possible that the length can be estimated without direct measurement by using population statistics. This is the measured distance the pulse wave travels during the PTT. The aortic pulse wave velocity (PWV) is this distance ($d_{artery}$) divided by the PTT as shown in the following formula.

$$PWV = \frac{d_{artery}}{PTT}$$

The PAT is a summation of the PEP and the PTT. The PEP starts at the beginning of ventricular contraction and ends with the start of ventricular ejection (when the aortic valve opens). The pulse transit time begins when the aortic valve opens and ends when the pressure wave reaches the distal measurement point. For blood pressure and aortic compliance, the ideal distal location is the end of the aorta, close to the start of the femoral artery.

The present disclosure provides a more accurate determination of aortic PWV using the bBCG (aortic valve opening—start of ventricular ejection) to a bPPG measured at the buttocks (close to the end of the aorta) as compared to prior disclosures. Thus, this measurement is dominated by the aorta characteristics, providing the most accurate estimate of aortic compliance and aortic blood pressure. This approach removes inaccuracies induced by measurement in the periphery, and by referencing the R-wave peak of the ECG.

Aortic compliance and blood pressure estimates can be based on the calculated PWV in accordance with the present disclosure using classical/clinically accepted standards.

In addition to measuring the BCG from the force sensors, the seat can also be used to estimate a user's weight. When a user sits on the seat, a certain percentage of their weight is on their feet. This percentage will be different based on body type and posture. If the user is leaning forward and resting their arms on the knees, a larger percentage of their weight will be on their feet. With respect to an integrated seat, since it is self-contained it can measure the weight present on the seat. Estimating or determining a user's seated posture is important for accurately estimating the user's weight. Machine learning can be used to estimate both posture and weight from the independently measured force sensors.

Thus, in an embodiment wherein the seat has a plurality of standoffs resting on a support surface it is important that the load present on the seat is only carried by the standoffs. The use of a floating hinge or pair of floating hinges to connect the seat to a toilet is an example of an embodiment which ensures that none of the load is present on the hinge, which could negatively impact the measurement accuracy and signal quality of both weight and BCG.

Direct integration of the BCG sensors into the seat's standoffs allows for complete integration of sensors into a standard seat. This is one way that such a technology is most likely to be adopted by users. This differs from similar devices that present a custom platform underneath an entire toilet, or additional legs/platform to carry the weight from the seat to a scale that surrounds the toilet.

Figure 6:
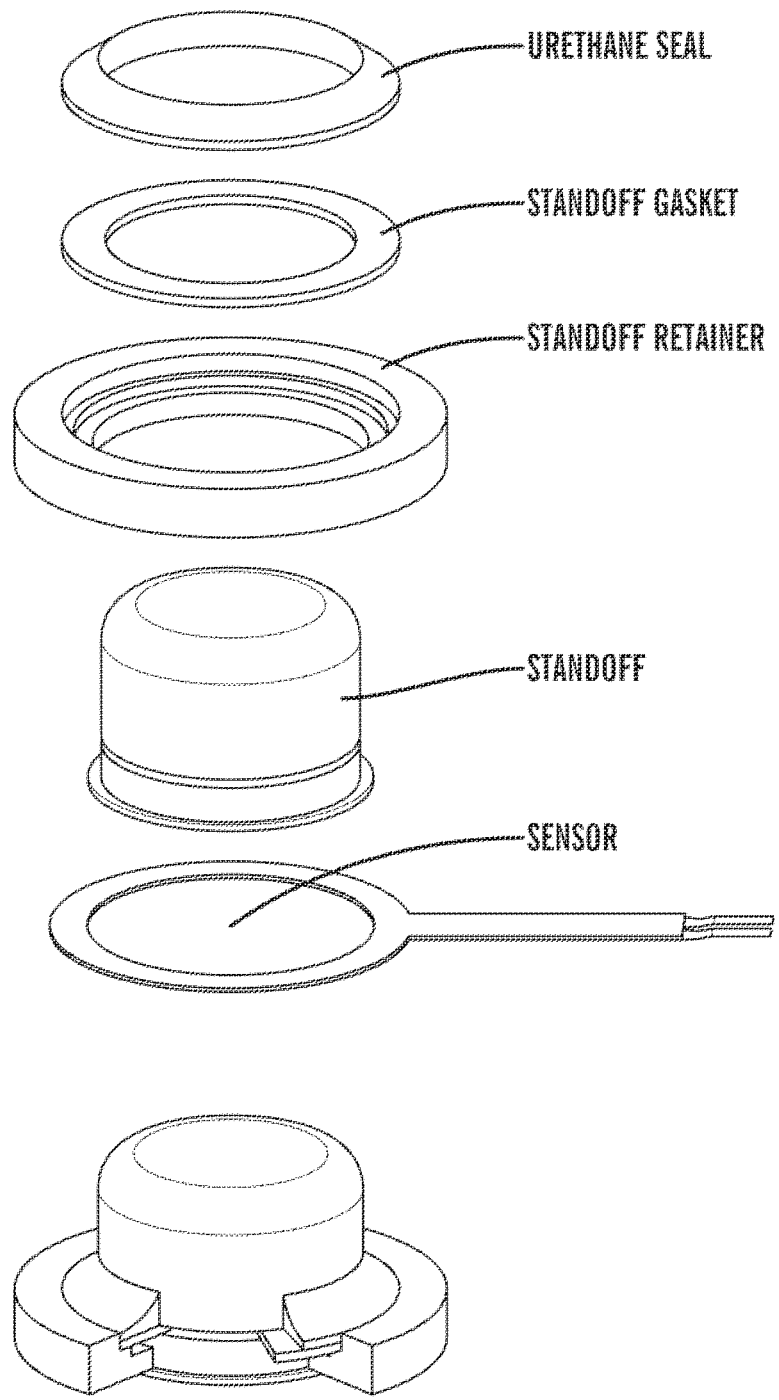
FIG. 6 illustrates an exploded view of a floating/sealed standoff and a perspective view illustrating a partial cutaway of a portion of the assembled floating/sealed standoff in accordance with an embodiment of the present disclosure.

One of the challenges of integrating the sensors into the standoff is that the standoff preferably translates all force to the BCG sensor and nowhere else. Furthermore, the standoff cannot bind; otherwise the BCG signal can be lost. FIG. 6 illustrates a floating/sealed standoff assembly in accordance with an embodiment of the present disclosure. This design incorporates a gasket encircling the standoff which mates with a retainer and urethane seal to fix the standoff to a cavity in the seat to accomplish these goals. Additionally, the standoffs are preferably waterproof and cleanable. This results in a system that is completely transparent to the end user. It is also important to note that any shape standoff can be used with this method.

Existing prior art BCG sensors and scales utilize sensor bridges to capture the BCG waveform. The bridge configuration is used to increase the signal to noise ratio and sensitivity of the sensor. This is very common in scales and other sensor systems. The downside of using a sensor bridge is that there is only one signal output for all four standoffs which does not allow for each standoff to be measured independently. While this allows for accurate BCG measurements under ideal circumstances (e.g., user standing upright on a scale while remaining perfectly still), it cannot be used to reliably measure the BCG of an individual sitting, for example on a toilet seat. The user's seated posture can impact the signal quality of the BCG and the waveform shape, as can motion artifacts.

In accordance with the present disclosure, separate BCG sensors can be used for each standoff. By measuring each sensor independently, the present method can use algorithms to estimate the posture and extract a more accurate and reliable BCG. This not only can improve the BCG signal quality, but it can also make the measurement more repeatable. This is an important feature of the embodiment since BCG force translation to the sensors changes based on the user's posture.

The use of multiple, e.g., four, independent sensors enable posture determination to assist in accurate determination of weight. As posture changes from an upright to leaning over position, more weight is carried by the feet to the floor. This is important for monitoring weight changes over time, especially for heart failure patients where rapid weight gain (water retention) is a predictive indicator of declining health.

Traditional prior art weight systems combine all force sensors into a single signal, such as with a Wheatstone bridge. Combining the signals in the analog domain reduces motion artifacts and increases signal to noise ratio ("SNR"). However, this results in a loss of posture information that is important in the present disclosure for accurate weight and BCG waveform analysis. In accordance with an embodiment of the present disclosure, rather than using a Wheatstone bridge, each sensor signal is captured independently and combined in software (utilizing posture information) to reduce motion artifacts and increase SNR. Combining four independent BCG channels into a single BCG signal uses the average between the four channels. Beat averaging can be used to further reduce noise, using the ECG R-wave peak for beat-to-beat feature alignment.

In accordance with an embodiment of the present disclosure, a pair of no-load bearing floating hinges allows the BCG to be measured with an integrated system in the toilet seat. A standard toilet seat has two hinges on the back of the seat that connects the seat and the lid to the toilet bowl. The BCG is stronger on the rear standoffs, as shown by subject testing. If part of the load on the seat were carried by the hinges, the BCG quality would significantly decrease. By removing the hinges as a load bearing point, two rear standoffs can be used to capture the majority of the BCG signal. A floating hinge also allows for more accurately estimating a user's weight, since the hinges bear none of the load.

Figure 5:
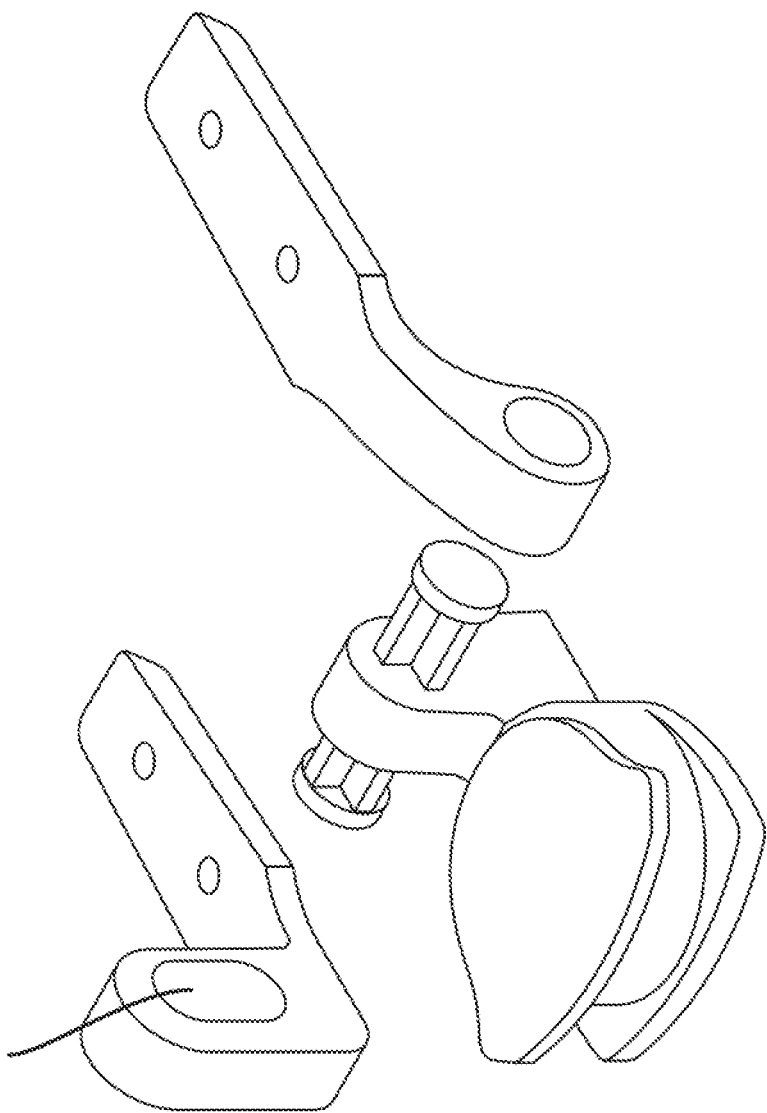
FIG. 5 illustrates an exploded view of a non-load bearing floating hinge in accordance with an embodiment of the present disclosure.

In one embodiment shown in FIG. 5, the floating hinge works by having an elongated slot that allows the entire seat to travel vertically in both directions. Note that the seat cover is still connected to the hinge in the standard way and is not floating independently from the seat. It is also important that the hinge design does not allow horizontal motion. This may exacerbate motion artifacts and can negatively impact the user's experience.

Figure 7:
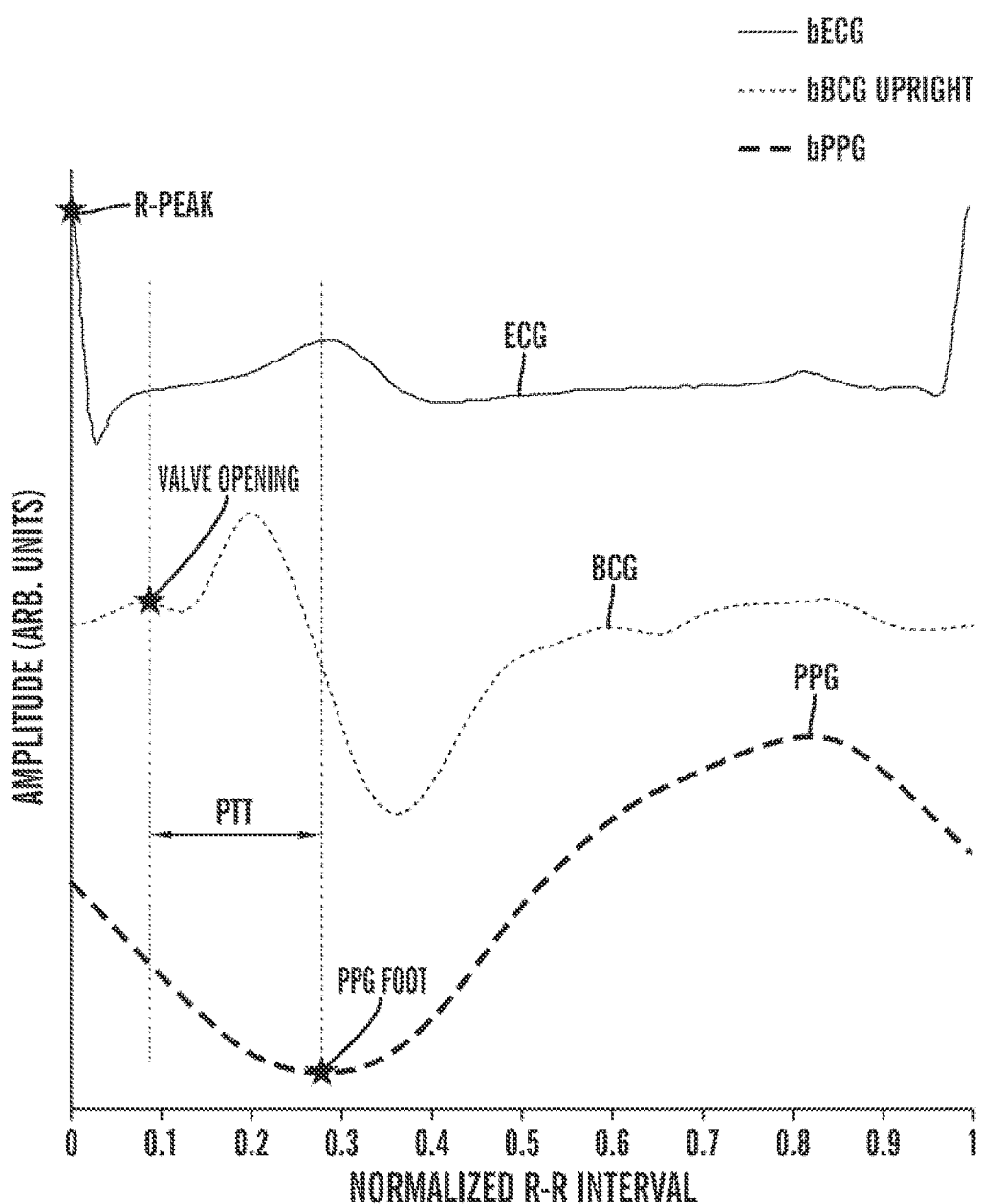
FIG. 7 is a graph of various waveforms generated from a seated individual in an upright position in accordance with an embodiment of the present disclosure.
Figure 8:
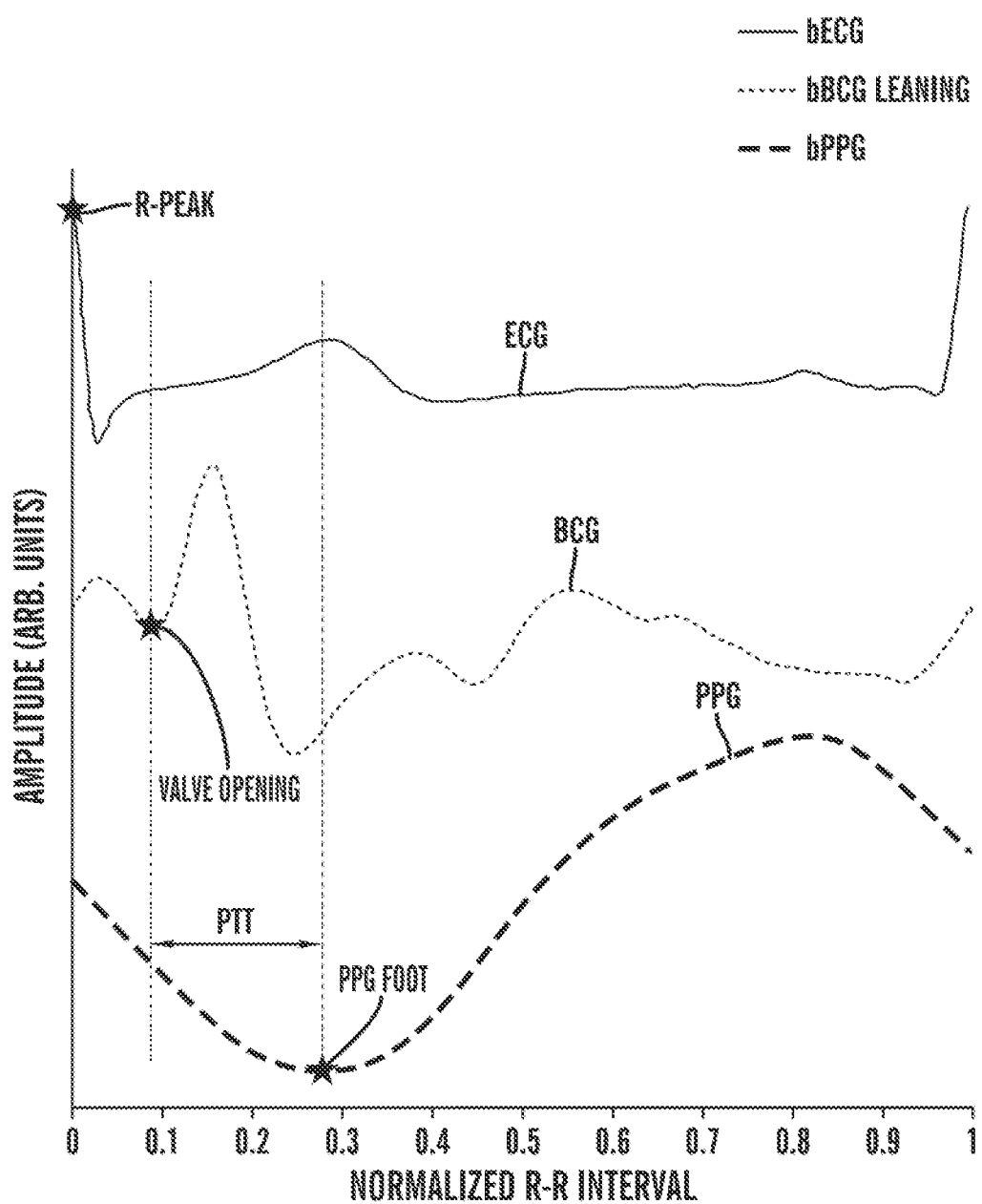
FIG. 8 is a graph of various waveforms generated from a seated individual in a leaning position in accordance with an embodiment of the present disclosure.

The BCG signature is impacted by posture since the force vector relative to gravity is changed. The difference between two postures, sitting upright and leaning forward are shown in FIGS. 7 and 8 along with a single R-R interval on the ECG. The morphology of each BCG signal changes with posture. Determination of posture based on, for example, analysis of the independent sensor readings is important to proper interpretation of the BCG waveform.

In an embodiment, determining weight and posture from BCG sensor readings includes the following steps: preprocessing of sensor readings, including mean reduction, scaling, data transformation to adjust for skewness in data; exploring higher order relations between sensor readings and output (weight); performing linear regression for estimating weight, and logistic regression for predicting posture on a training dataset containing sensor readings and subjects' weight and posture. In both regressions, all of the four sensor readings, sensor interaction terms and higher order features (as explored in the previous step) are fed to the regression block for accurate estimation of weight and posture.

An embodiment of the present disclosure provides the automatic integration of a simulated Valsalva maneuver with BM. The Valsalva maneuver, where a subject forcedly exhales against a fixed pressure (or by keeping the mouth and nose closed), induces a transient increase in intrathoracic pressure that can provide estimates of changes in both stroke volume and pre-ejection period based on ECG and BCG measures. A lack of change in stroke volume during this strain phase of the Valsalva maneuver has been observed in patients with pulmonary congestion and reduced left ventricular ejection fraction suggesting potential for early detection with routine monitoring. Additionally, the Valsalva maneuver may also be useful in evaluating the risk of ventricular tachyarrhythmias and the efficacy of drug treatment in patients with long-QT syndrome.

By integrating cardiac instrumentation with a toilet seat, cardiac measurements can be captured during a BM. When the user is straining during a BM, it is very similar to the Valsalva maneuver, and thus, provides a simulated Valsalva maneuver.

Methods for determination of aortic valve opening from the BCG for different postures.

The BCG can be measured from a plurality of sensors in a seat. The static signal from each sensor can be used to determine posture of the subject. For example, higher relative signals on the forward sensors is indicative of the subject leaning forward, with the ratio of the forward to back sensors indicative of the posture angle. In another example, the subject height, weight, age and/or gender are used in conjunction with the static signals for a more accurate determination of posture. In another example, statistical analysis (e.g., machine learning) of signals gathered at different postures across a population can be used to provide a posture estimate from the obtained signals.

Posture can also be determined by additional methods including user entry of posture (e.g., position 1, 2, or 3 representing angles of approximately 90 degrees, 60 degrees, or 45 degrees); a video camera and image processing to determine torso outline and relative angle between torso and legs; and a distance sensor integrated into the toilet seat cover. The waveform characteristics of the average BCG signal can be used to determine posture. During a training phase, data can be collected with subjects in different known postures. Waveform characteristics associated with each posture can be determined and used for future posture determination based on average BCG waveform analysis.

Posture information can be used to determine temporal segments for specific BCG analysis where the subject has consistent posture. Aortic valve opening is then determined from a combination of the dynamic BCG signal and the subject posture.

In an embodiment, the specific BCG waveform feature to be extracted is posture dependent. In an upright posture (alpha approx. 90°) aortic valve opening is associated with the first upward peak of the BCG waveform from the beginning of the cardiac cycle as shown in FIG. 7, by way of example only. In a leaning forward position (alpha approx. 50°) aortic valve opening is associated with the first downward peak of the BCG waveform from the beginning of the cardiac cycle as shown in FIG. 8, by way of example only. Other features or posture-dependent fractional distances between neighboring features may also be used. The specific BCG features can be from the BCG waveform, or from a transformed BCG such as the $1^{st}$, $2^{nd}$, $3^{rd}$, etc. derivatives or integrals.

Figure 4:
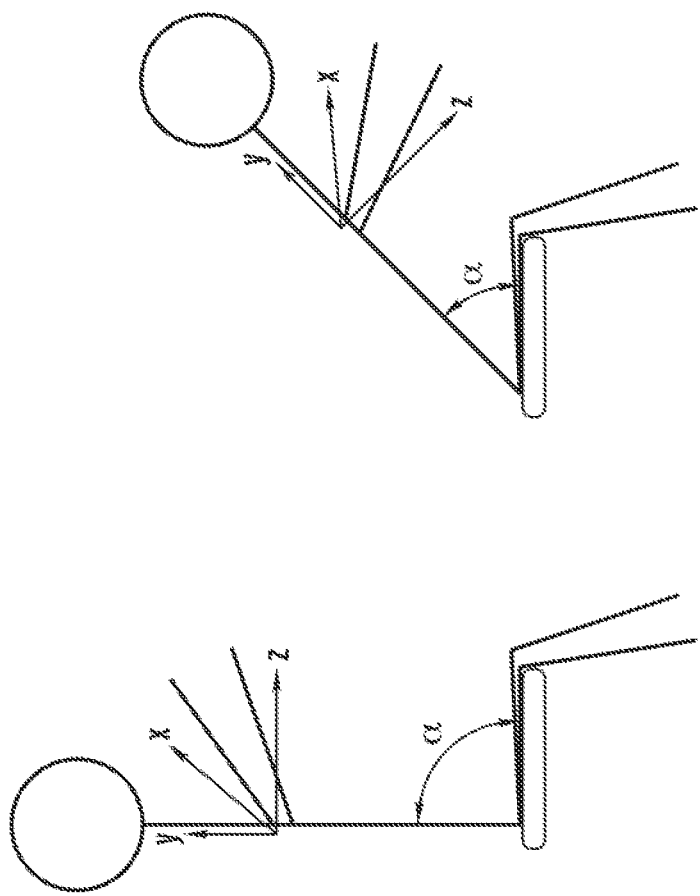
FIG. 4 is a diagram depicting various posture positions of a seated individual.

In another embodiment, a leaning forward BCG waveform is transformed to an upright BCG waveform based on posture. Posture is the angle from the seat platform to the torso of a seated individual. The BCG waveform is determined for the y and z directions as shown in FIG. 4. A model is generated for transformation of these primary waveforms to a new waveform consistent with a potential posture (alpha dependent). This model uses vector analysis of force transformations and superposition to create the new waveform. In another embodiment, torque is incorporated into the model based on subject height, weight, age and/or gender and an estimate of the location of the heart. The inverse model is applied to the captured BCG dynamic signals based on determined posture to create an equivalent upright waveform. The upright waveform feature recognition is applied to the equivalent upright waveform to determine aortic valve opening.

In another embodiment, the features to be extracted are determined by simultaneous BCG measurements with a gold-standard aortic valve opening measurement. A database containing correlation of the angle between the seat and the torso of a seated individual with the bBCG data corresponding to the opening of the aortic valve can be established. The correlation of specific BCG features to aortic valve opening can be determine for a range of postures, resulting in a database such as a lookup table indicating which feature should be chosen based on the current posture of the seated individual. In one example, the lookup table can be created for a population (e.g., entire population, healthy population, heart failure population, etc.) using statistics from a posture study across the desired population. In another example, this is done on a population with key features classified according to subject height, weight, age and/or gender. In another example, the lookup table can be created for each individual subject based an individualized feature correlation to aortic valve opening on a per-subject basis.

This table can be created by correlating specific BCG features directly (or with a time offset) to the simultaneous aortic valve opening gold standard measurement. The time offset could be a constant, or an equation based on physiologic intervals such as heart rate, or a combination of the two. The specific BCG features can be from the BCG itself, or from a transformed BCG such as the $1^{st}$, $2^{nd}$, $3^{rd}$, etc. derivatives or integrals. The subject sits on the seat containing the BCG sensors while measuring the time of aortic valve opening. This can be repeated for multiple postures (from upright to full leaning forward as when resting elbows on knees) with known angles between the torso and the seating platform. In one example, the time of aortic valve opening can be determined through transthoracic echocardiography captures of pulse wave Doppler, tissue strain, and aortic valve imaging measured simultaneously and time synchronized with the BCG. In another example, the time of aortic valve opening can be determined using a time synchronized measure of impedance cardiography. In a third example, the time of aortic valve opening can be determined using an aortic flow rate sensor measuring the start of systolic ejection, when time synchronized with the BCG. The gold-standard and BCG waveforms can be time synchronized through acquisition through the same data acquisition system, application of a third signature that is picked up in both the gold-standard and BCG waveforms, or by using a surrogate reference point for both measures such as the ECG R-wave.

The time corresponding to a specific BCG waveform feature can be determined for each posture. In one example, this is done on a beat by beat basis and the results averaged. In another example, the waveform is first normalized to account for different R-R intervals (heart rate variability), and then the BCG (and ECG) beat waveforms are averaged to create an average waveform before extracting the feature time points. This information can be used to create the aforementioned lookup table, which can be used to determine the time of aortic valve opening using the BCG.

Method for Determination of the PPG feature for pulse wave arrival in the PTT calculation.

A plethysmograph is obtained on the individual at a distal point to determine changes in blood volume or pressure associated with arrival of the pressure wave associated with ventricular ejection. In one example this is done optically using a photodiode and an emitter (photoplethysmogram or PPG). In another example, impedance techniques are used to locally determine changes in blood volume. In another example, a pressure or force sensor is used in a tonometry mode to detect pulse arrival.

The time based waveform is analyzed to extract the time of a specific waveform feature. In one example, this is the onset of the wave (or foot) as shown in FIG. 7, although other features may be used. Other features or fractional distances between neighboring features may also be used. Features associated with the derivatives (e.g., $1^{st}$, $2^{nd}$, $3^{rd}$, etc.) of the PPG waveform may also be used. In one example, this is done on a beat by beat basis and the results averaged. In another example, the waveform is first normalized to account for different R-R intervals (heart rate variability), and then the PPG (and ECG) beat waveforms are averaged to create an average waveform before extracting the feature time points.

Method for Determination of the PWV based on the BCG and PPG waveforms.

The length of the artery from the aortic valve to a selected end point along the artery (AL) can be determined based on direct subject measurement (external). Measurements are done on an individual in a seated position. The distance between the sternal notch (SN) and the sternal angle (SA) is measured, either directly or by reference to the seating platform top (B). The distance between sternal angle (SA) and aortic valve (AV) is measured, e.g., via ultrasound imaging. The distance between sternal notch and aortic arch (AA) is measured, e.g., via ultrasound imaging. The approximate artery length (AL) is calculated using the following equation:

$$AL=[AV \text{ to } AA \text{ distance}]+[AA \text{ to } B \text{ distance}] AL \cong [(SA-AV)+(SN-SA)-(SN-AA)]+[(SN-B)-(SN-AA)]$$

In another embodiment, population statistics based on height, weight, age and/or gender are used in place of a subject specific measurement. The time difference between the aortic valve opening feature on the BCG waveform and the pulse arrival feature on the distal PPG waveform determines the pulse transit time (PTT). The aligned BCG and PPG waveform extracted time points can be used directly, or each can be referenced to the ECG R-wave. The pulse wave velocity (PWV) is calculated by dividing the AL by the PTT.

The disclosure will be further illustrated with reference to the following specific examples. It is understood that these examples are given by way of illustration and are not meant to limit the disclosure or the claims to follow.

EXAMPLES

The following experimental protocol, conditions and instrumentation were used in each of the examples. The user was instructed to remove clothing and put on a hospital gown. The user was instructed to sit on the seat with complete skin contact. The weight, PPG, ECG, and BCG waveforms were simultaneously captured using a NI CompactRio system with LabView for 2.5 minutes. The signals were analyzed in MATLAB in order to locate the desired features in the signal.

Figure 9:
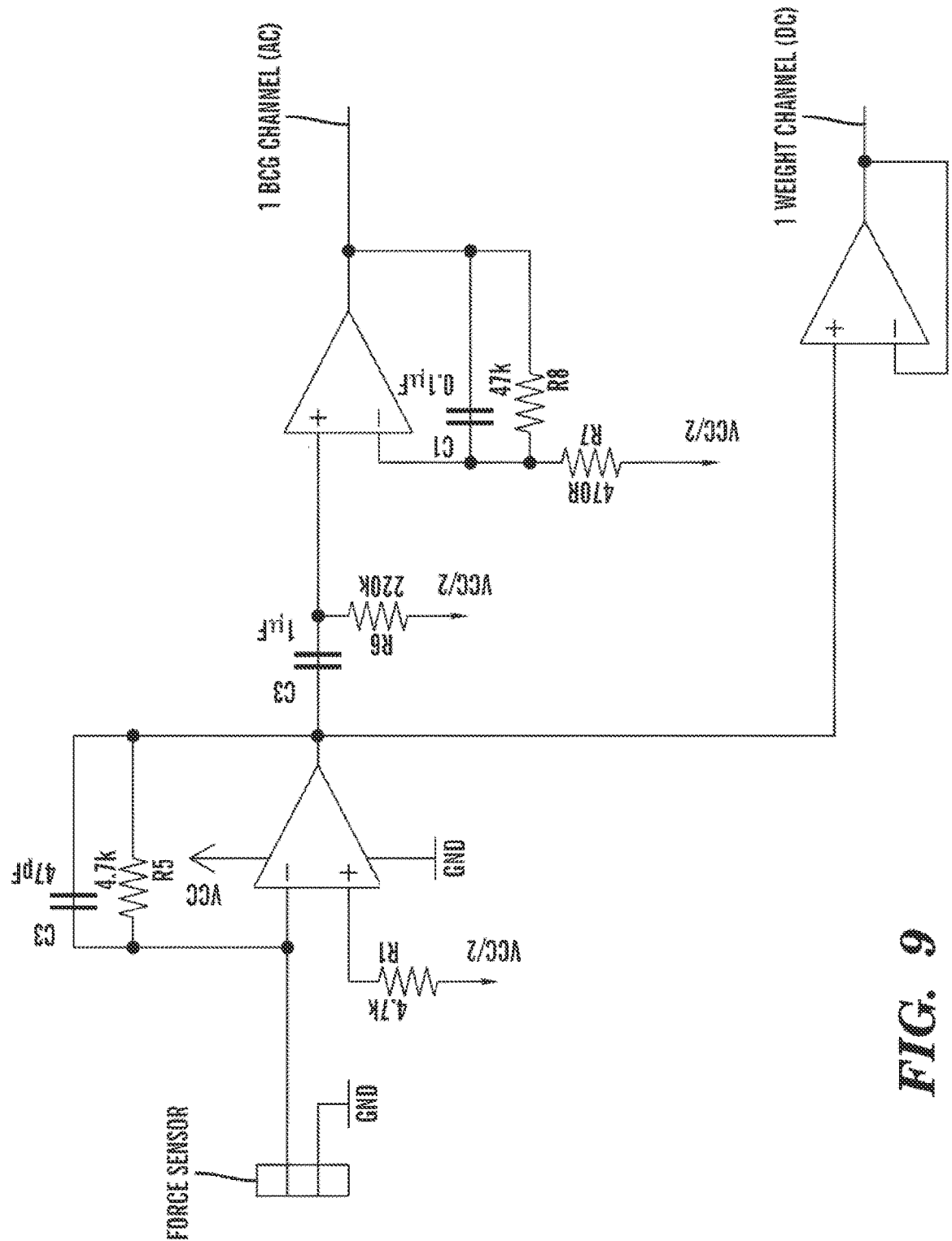
FIG. 9 is a schematic of a BCG force sensor in accordance with an embodiment of the present disclosure.

The BCG system uses four independent piezoresistive sensors (Flexi Force sensors from Tekscan). The interface schematic is shown in FIG. 9. The signal takes two paths, one for the BCG and the other for the weight. The weight is buffered and then directly captured by the data acquisition system. A low-pass filter is used to reduce high frequency noise and a high-pass filter is used to remove the large DC offset due to the subject's weight.

The PPG sensor uses an IR LED with a matched photodiode. The photodiode's current is converted to a voltage using a transimpedance amplifier (TIA). The DC offset is removed and then the signal is low-pass filtered to isolate the PPG signal.

The ECG sensor has three electrodes. The two rear electrodes were used as the inputs to a differential amplifier. The third electrode is connected to the circuit ground and is located on the right side of the user on the front of the seat. The instrumentation used is built into the Biopac data acquisition system.

All of the instrumentation is captured on a LabView data acquisition system. Signal processing techniques are then used to locate the BCG feature associated with aortic valve opening. Similar techniques are used to locate the onset of the PPG waveform (this is called the PPG foot).

Example 1

PWV Measurement of Individual Sitting in Upright Position

Determination of the PTT when a subject is in an upright sitting position, i.e. an angle of approximately 90° between the seat platform and the torso of the subject. The following example takes place in a lab setting at room temperature with a healthy individual (subject) with no history of cardiovascular disease. The subject is told to sit upright with skin contact on a toilet seat that contains the following sensors: 4 BCG channels; PPG; and ECG. The sensor locations are those shown in FIGS. 1 and 2.

A 2.5 minute long recording is captured using a National Instruments data acquisition system. Each channel is captured at 1000 samples per second and is time synchronized. Once the recording is finished, the subject is no longer needed and the signals can be analyzed. The R-peak in each heart beat is located using a standard ECG delineation method. For example, "A Real-Time QRS Detection Algorithm" by Pan and Tompkins. In the example shown in FIG. 7 the average R-R interval was found to be 0.603 seconds, resulting in a heart rate of 99.5 BPM.

A single average PPG beat is found using the following beat averaging technique. Each PPG beat is defined as the wave between each consecutive R-peak. After locating each PPG beat, they are all resampled so that they have the same length (in this example, the length will be the average R-R interval multiplied by the sample rate). Once all of the PPG beats are of the same length, they are averaged together on a sample-by-sample basis. The resulting waveform is the averaged PPG beat.

The onset of the PPG (PPG foot) is determined to be the minimum of the average beat. A single BCG waveform is calculated from the four raw BCG channels by simply averaging them together. This isolates the BCG in the y direction when sitting upright (see FIG. 4). A single average BCG beat is determined using the same method as was done with the PPG.

The aortic valve opening is located on the BCG between the ECG Qwave and the PPG foot. When the subject is sitting upright, the opening of the aortic valve is determined to be the first BCG peak after the Qwave.

The pulse transit time (PTT) can be calculated by finding the interval between the aortic valve opening ($AV_{open}$) and the PPG foot ($PPG_{foot}$). The time difference is normalized to the R-R interval (($RR_{interval}$), so the actual PTT can be calculated by multiplying the relative time interval with the R-R interval.

$$PTT = (AV_{open} - PPG_{foot}) * RR_{interval}$$

In this example, the PTT for sitting upright is 152 milliseconds. The length of the arterial segment between the aortic valve and the selected end point (AL) was determined to be 0.94 meters. The PWV is calculated according to the formula PWV=AL/PTT to be 6.18 m/s.

Example 2

PWV Measurement of Individual Sitting In Leaning Forward Position

Determination of the PTT when a subject is in a leaning forward sitting position, i.e. an angle of approximately 50° between the seat platform and the torso of the subject. The following example takes place in a lab setting at room temperature with a healthy individual (subject) with no history of cardiovascular disease. The subject is told to sit in a leaning forward position with skin contact on a toilet seat that contains the following sensors: 4 BCG channels; PPG; and ECG. The sensor locations are those shown in FIGS. 1 and 2.

A 2.5 minute long recording is captured using a National Instruments data acquisition system. Each channel is captured at 1000 samples per second and is time synchronized. Once the recording is finished, the subject is no longer needed and the signals can be analyzed. The R-peak in each heart beat is located using a standard ECG delineation method. For example, "A Real-Time QRS Detection Algorithm" by Pan and Tompkins. In the example shown in FIG. 8 the average R-R interval was found to be 0.603 seconds, resulting in a heart rate of 99.5 BPM.

A single average PPG beat is found using the following beat averaging technique. Each PPG beat is defined as the wave between each consecutive R-peak. After locating each PPG beat, they are all resampled so that they have the same length (in this example, the length will be the average R-R interval multiplied by the sample rate). Once all of the PPG beats are of the same length, they are averaged together on a sample-by-sample basis. The resulting waveform is the averaged PPG beat.

The onset of the PPG (PPG foot) is determined to be the minimum of the average beat. A single BCG waveform is calculated from the four raw BCG channels by averaging them together. This isolates the BCG in the y direction when sitting upright (see FIG. 4). A single average BCG beat is determined using the same method as was done with the PPG.

The aortic valve opening is located on the BCG between the ECG Q-wave and the PPG foot. When the subject is leaning forward at an angle of approximately 50°, the opening of the aortic valve corresponds to the first trough before the main BCG peak.

The pulse transit time (PTT) can be calculated by finding the interval between the aortic valve opening ($AV_{open}$) and the PPG foot ($PPG_{foot}$). The time difference is normalized to the R-R interval ($RR_{interval}$), so the actual PTT can be calculated by multiplying the relative time interval with the R-R interval.

$$PTT=(AV_{open}-PPG_{foot})*RR_{interval}$$

In this example, the PTT for sitting leaning forward at an angle of approximately 50° is 150 milliseconds. The length of the arterial segment between the aortic valve and the selected end point (AL) was determined to be 0.94 meters. The PWV is calculated according to the formula PWV=AL/PTT to be 6.27 m/s.

Example 3

Measurement of Physiological Changes Associated with a BM

The subject is instructed to take a BM while on the fully integrated toilet seat. The interval during the BM is determined by the subject on a handheld device. The parameters that are associated with the Valsalva maneuver, such as the QT interval, are extracted for both the BM state and non-BM state.

Taking a bowel movement (BM) allows more advanced diagnosis on the integrated toilet seat.

Method 1—Instructed

User is instructed to keep their mouth and nasal cavity closed while attempting to forcedly exhale while sitting on the seat.

The Valsalva maneuver is performed for 5 seconds.

All of the signals previous mentioned are captured and analyzed.

Method 2—Automatic

User sits on the seat in their home to perform a BM.

There will be a period during BM that will be recognized as the simulated Valsalva.

Automatic analysis will be used to determine the physiological differences between the resting state and simulated Valsalva state.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. An apparatus, comprising:
a seat supportable on a surface of a base, the seat including a plurality of standoffs disposed on a bottom side of the seat and configured to rest on the surface of the base;
a plurality of force sensors including a force sensor disposed at each of the plurality of standoffs, the plurality of force sensors configured to generate one or more signals based on changes in loads applied by a subject seated to a top side of the seat, the one or more signals including forward signals and back signals associated with force sensors disposed on a forward portion and a back portion of the seat, respectively;
a coupler configured to couple the seat to the base in a non-load bearing configuration such that a majority of the loads applied by the subject are transferred to the base via the plurality of standoffs, the coupler configured to allow the seat to move vertically relative to the base while preventing the seat from moving horizontally relative to the base, and
a processor operatively coupled to the plurality of force sensors and configured to:
receive information indicative of the one or more signals from the plurality of force sensors; and
determine a posture of the subject seated on the top side of the seat based on a ratio of the forward to back signals.

2. The apparatus of claim 1, wherein the coupler includes an elongated slot.

3. The apparatus of claim 1, further comprising a seat cover, the coupler further being configured to couple the seat cover to the seat and the base.

4. The apparatus of claim 1, wherein each force sensor of the plurality of force sensors is configured to independently generate a signal based on a change measured by that sensor in the loads applied by the subject.

5. The apparatus of claim 1, wherein the processor is further configured to:
generate a ballistocardiogram (BCG) or weight signal over time of the subject based on the information indicative of the one or more signals; and
determine physiological information of the subject based at least on the BCG or weight signal.

6. The apparatus of claim 5, wherein the processor is further configured to:
determine the physiological information of the subject based on the BCG or weight signal and the posture of the subject.

7. The apparatus of claim 6, wherein the processor is configured to determine the physiological information of the subject by:
transforming the BCG or weight signal based on the posture of the subject;
extracting one or more features from the BCG or weight signal after transforming the BCG or weight signal; and
determining the physiological information based on the one or more features extracted from the BCG or weight signal.

8. The apparatus of claim 5, wherein the processor is further configured to:
receive a signal representing an electrocardiogram (ECG) of the subject,
the processor configured to determine the physiological information of the subject based on the BCG or weight signal and the ECG signal.

9. The apparatus of claim 8, wherein the processor is configured to determine the physiological information by:
identifying, based on the ECG signal, a window in the BCG or weight signal containing a feature that is associated with an opening of an aortic valve of the subject; and
determining the physiological information based on a timing of the opening of the aortic valve.

10. The apparatus of claim 1, wherein the processor is a processor associated with a system that is remote from the plurality of force sensors.

11. An apparatus, comprising:
a seat supportable on a surface of a base, the seat including a plurality of standoffs disposed on a bottom side of the seat and configured to rest on the surface of the base;
a plurality of force sensors including a force sensor disposed at each of the plurality of standoffs, the plurality of force sensors configured to generate one or more signals based on changes in loads applied by a subject seated to a top side of the seat;

a coupler configured to couple the seat to the base such that the seat can move relative to the base; and a processor operatively coupled to the plurality of force sensors, the processor configured to:

receive information indicative of the one or more signals from the plurality of force sensors;

generate a first ballistocardiogram (BCG) or weight signal over time of the subject based on the information indicative of the one or more signals, the first BCG or weight signal associated with a non-upright posture;

determine a posture of the subject;

transform the first BCG or weight signal into a second BCG or weight signal associated with an upright posture based on the posture of the subject; and determine physiological information of the subject based on the second BCG or weight signal.

12. The apparatus of claim 11, wherein the processor is configured to determine the posture of the subject by:

extracting one or more features from the first BCG or weight signal; and processing the one or more features using a model trained to identify the posture of the subject, the model having been trained using previously collected BCG or weight signals of subjects in different known postures.

13. The apparatus of claim 11, wherein the processor is configured to determine the posture of the subject based on a user entry of posture information.

14. The apparatus of claim 11, wherein the processor is further configured to extract temporal segments of the first BCG or weight signal associated with periods of time in which the posture of the subject is consistent.

15. The apparatus of claim 11, wherein each force sensor of the plurality of force sensors is configured to independently generate a signal based on a change measured by that sensor in the loads applied by the subject.

16. The apparatus of claim 11, wherein the physiological information includes at least one of: a stroke volume associated with one or more heartbeats of the subject, a pulse transit time associated with one or more heartbeats of the subject, a pulse wave velocity associated with one or more heartbeats of the subject, or blood pressure.

17. The apparatus of claim 11, wherein the processor is configured to determine the posture of the subject based on information received from a distance sensor disposed on a lid facing the subject.

18. An apparatus, comprising:

a seat supportable on a surface of a base;

a plurality of force sensors configured to generate one or more signals based on changes in loads applied by a subject seated to the seat;

a coupler configured to couple the seat to the base such that the seat can move relative to the base; and a processor operatively coupled to the plurality of force sensors, the processor configured to:

receive information indicative of the one or more signals from the plurality of force sensors;

generate a ballistocardiogram (BCG) or weight signal over time of the subject based on the information indicative of the one or more signals;

determine a time associated with an opening of an aortic valve of the subject based on the BCG or weight signal;

determine a pulse transit time (PTT) between the time associated with the opening of the aortic valve and a time associated with an arrival of a pulse wave initiated by the opening of the aortic valve at a predefined point along an artery of the subject; and determine a pulse wave velocity (PWV) of the subject based on the PTT and a length of an arterial segment between the aortic valve and the predefined point.

19. The apparatus of claim 18, wherein the processor is further configured to determine a posture of the subject seated to the seat, the processor configured to determine the time associated with an opening of the aortic valve based on the BCG or weight signal and the posture.

20. The apparatus of claim 18, wherein the plurality of force sensors includes a force sensor disposed near the predefined point along the artery of the subject, the predefined point being located in a portion of the buttocks or the upper thigh of the subject.

21. The apparatus of claim 18, wherein the processor is further configured to:

receive a signal representing an electrocardiogram (ECG) of the subject, the processor configured to determine the time associated with an opening of the aortic valve based on the BCG or weight signal and the ECG signal.

22. The apparatus of claim 18, wherein the processor is further configured to determine the length of the arterial segment based on population statistics associated with the subject that are dependent on a height, a weight, an age, or a gender of the subject.

23. An apparatus, comprising:

a seat supportable on a surface of a base, the seat including a plurality of standoffs disposed on a bottom side of the seat and configured to rest on the surface of the base;

a plurality of force sensors including a force sensor disposed at each of the plurality of standoffs, the plurality of force sensors configured to generate one or more signals based on changes in loads applied by a subject seated to a top side of the seat;

a coupler configured to couple the seat to the base such that the seat can move relative to the base; and a processor operatively coupled to the plurality of force sensors and configured to:

receive information indicative of the one or more signals from the plurality of force sensors;

generate a ballistocardiogram (BCG) or weight signal over time of the subject based on the information indicative of the one or more signals;

determine a posture of subject; and determine physiological information of the subject based on the BCG or weight signal and the posture of the subject.

24. The apparatus of claim 23, wherein the processor is configured to determine the posture of the subject by:

extracting one or more features from the BCG or weight signal; and processing the one or more features using a model trained to identify the posture of the subject, the model having been trained using previously collected BCG or weight signals of subjects in different known postures.

25. The apparatus of claim 23, wherein the processor is configured to determine the posture of the subject based on a user entry of posture information.

26. The apparatus of claim 23, wherein the physiological information includes at least one of: a stroke volume associated with one or more heartbeats of the subject, a pulse transit time associated with one or more heartbeats of the subject, a pulse wave velocity associated with one or more heartbeats of the subject, or blood pressure.

27. The apparatus of claim 23, wherein the processor is a processor associated with a system that is remote from the plurality of force sensors.

\* \* \* \* \*